United States Patent
Rudko et al.

(10) Patent No.: US 7,377,916 B2
(45) Date of Patent: ***May 27, 2008

(54) ENDOVASCULAR TISSUE REMOVAL DEVICE

(75) Inventors: Robert I. Rudko, Holliston, MA (US); Mark R. Tauscher, Medfield, MA (US); Richard P. Yeomans, Jr., Medway, MA (US)

(73) Assignee: PLC Medical Systems, Inc., Franklin, MA (US)

( * ) Notice: Subject to any disclaimer, the term of this patent is extended or adjusted under 35 U.S.C. 154(b) by 349 days.

This patent is subject to a terminal disclaimer.

(21) Appl. No.: 10/753,693

(22) Filed: Jan. 7, 2004

(65) Prior Publication Data

US 2004/0260276 A1 Dec. 23, 2004

Related U.S. Application Data

(63) Continuation-in-part of application No. 10/600,175, filed on Jun. 20, 2003.

(51) Int. Cl.
*A61B 18/18* (2006.01)
(52) U.S. Cl. ............................................. 606/15; 606/7
(58) Field of Classification Search ............... 606/7, 606/10, 14–19; 607/88, 89; 128/898
See application file for complete search history.

(56) References Cited

U.S. PATENT DOCUMENTS

| | | | |
|---|---|---|---|
| 467,852 A | 1/1892 | Buckelew | |
| 1,858,544 A | 5/1932 | Erickson | |
| 2,267,110 A | 12/1941 | Kinley et al. | |
| 3,271,869 A | 9/1966 | Ratner | |
| 3,505,987 A | 4/1970 | Heilman | |
| 3,533,166 A | 10/1970 | Pino, Jr. | |
| 3,555,689 A | 1/1971 | Cubberly, Jr. | |
| 3,772,794 A | 11/1973 | Hopler, Jr. | |
| 4,213,246 A | 7/1980 | Stevens | |
| 4,407,157 A | 10/1983 | Lichtenberg | |
| 4,411,648 A | 10/1983 | Davis et al. | |
| 4,587,975 A | 5/1986 | Salo et al. | |
| 5,074,871 A | 12/1991 | Groshong | |
| 5,171,248 A | 12/1992 | Ellis | |
| 5,176,693 A | 1/1993 | Pannek, Jr. | |
| 5,238,005 A | 8/1993 | Imran | |
| 5,275,169 A | 1/1994 | Afromowitz et al. | |
| 5,356,382 A | 10/1994 | Picha et al. | |
| 5,366,490 A | 11/1994 | Edwards et al. | |
| 5,370,685 A | 12/1994 | Stevens | |
| 5,398,691 A | 3/1995 | Martin et al. | |
| 5,411,552 A | 5/1995 | Andersen et al. | |
| 5,428,903 A | 7/1995 | Pocci | |

(Continued)

OTHER PUBLICATIONS

Cardima *Naviport Deflectable Tip Guiding Catheter* Brochure, Oct. 2001.

(Continued)

*Primary Examiner*—Ahmed M Farah
(74) *Attorney, Agent, or Firm*—Iandiorio Teska & Coleman (57) ABSTRACT

An endovascular tissue removal system including an expandable mechanism introduceable to the ventricular side of a valve to support the leaflets of the valve in a closed position and a tissue removal device advanceable to the leaflets and configured to resect the leaflets as they are supported by the expandable mechanism.

29 Claims, 12 Drawing Sheets

U.S. PATENT DOCUMENTS

| | | |
|---|---|---|
| 5,465,732 A | 11/1995 | Abele |
| 5,499,995 A | 3/1996 | Teirstein |
| 5,545,214 A * | 8/1996 | Stevens .................. 606/191 |
| 5,554,185 A | 9/1996 | Block et al. |
| 5,562,665 A | 10/1996 | Young |
| 5,607,462 A | 3/1997 | Imran |
| 5,693,043 A * | 12/1997 | Kittrell et al. ............. 606/15 |
| 5,725,523 A * | 3/1998 | Mueller ..................... 606/15 |
| 5,728,123 A * | 3/1998 | Lemelson et al. ........... 604/22 |
| 5,830,210 A * | 11/1998 | Rudko et al. ............... 606/15 |
| 5,840,081 A | 11/1998 | Andersen et al. |
| 5,885,244 A | 3/1999 | Leone et al. |
| 5,899,915 A | 5/1999 | Saadat |
| 5,957,916 A * | 9/1999 | Jeevanandam et al. ....... 606/15 |
| 6,010,511 A | 1/2000 | Murphy |
| 6,023,638 A * | 2/2000 | Swanson ................... 600/510 |
| 6,033,359 A | 3/2000 | Doi |
| 6,056,743 A * | 5/2000 | Ellis et al. .................. 606/15 |
| 6,081,737 A | 6/2000 | Shah |
| 6,106,515 A | 8/2000 | Winston et al. |
| 6,110,200 A | 8/2000 | Hinnenkamp |
| 6,168,614 B1 | 1/2001 | Andersen et al. |
| 6,287,321 B1 | 9/2001 | Jang |
| 6,423,055 B1 | 7/2002 | Farr et al. |
| 6,425,916 B1 | 7/2002 | Garrison et al. |
| 6,450,976 B2 | 9/2002 | Korotko et al. |
| 6,485,485 B1 | 11/2002 | Winston et al. |
| 6,517,515 B1 | 2/2003 | Eidenschink |
| 6,560,889 B1 | 5/2003 | Lechen |
| 6,616,629 B1 * | 9/2003 | Verin et al. ............ 604/101.05 |
| 6,656,204 B2 * | 12/2003 | Ambrisco et al. .......... 606/200 |
| 6,764,453 B2 | 7/2004 | Meier |
| 6,767,362 B2 * | 7/2004 | Schreck .................... 623/2.11 |
| 6,908,478 B2 | 6/2005 | Alferness et al. |
| 2002/0058995 A1 | 5/2002 | Stevens |
| 2002/0095116 A1 | 7/2002 | Strecter |

OTHER PUBLICATIONS

U.S. Appl. No. 10/600,175, filed Jun. 20, 2003, Rudko et al.
U.S. Appl. No. 10/628,794, filed Jul. 28, 2003, Rudko et al.
U.S. Appl. No. 10/447,532, filed May 29, 2003, Rudko et al.

* cited by examiner

ENDOVASCULAR TISSUE REMOVAL DEVICE

RELATED APPLICATIONS

This application is a continuation-in-part application of U.S. patent application Ser. No. 10/600,175 filed on Jun. 20, 2003.

FIELD OF THE INVENTION

This invention relates to endovascular aortic valve replacement.

BACKGROUND OF THE INVENTION

Currently, replacement of a malfunctioning heart valve is accomplished by a major open-heart surgical procedure requiring general anesthesia, full cardio-pulmonary bypass with complete cessation of cardio-pulmonary activity, and a long period of hospitalization and recuperation. In most cases, the native valve is resected (cut-out) and the replacement valve then installed.

As an alternative to open heart surgery, those skilled in the art have attempted to devise systems for endovascular heart valve replacement to overcome the disadvantages associated with open-heart surgery. U.S. Pat. No. 5,370,685, for example, discloses a procedure device capsule connected to a tube and delivered to the site via a guide wire introduced in the femoral artery of a patient. The device capsule houses an expandable barrier attached to balloon segments. Once the guide wire is removed and the barrier is expanded, a tissue cutting blade assembly is advanced in the tube and rotated by a DC motor to resect the existing valve. The barrier traps any debris cut by the tissue cutting blade assembly. Tissue is then suctioned out via the tube. Next, the cutting blade assembly is removed, the barrier balloons are deflated, and the barrier is brought back into the capsule and the capsule itself is removed.

Then, a valve introducer capsule is advanced to the site. The capsule houses a replacement valve and includes a pusher disk and inflatable balloon segments. After the balloon segments are inflated, the pusher disk pushes the replacement valve into position and a mounting balloon is used to expand the replacement valve and to secure it in place. Then, the introducer capsule is removed. The '685 patent is hereby incorporated herein. See also U.S. Pat. Nos. 5,545,214; 6,168,614; 5,840,081; 5,411,552; 5,370,685; and published Patent Application No. U.S. 2002/0058995 A1. These patents are also incorporated herein.

One problem with such a system is that the tissue cutting blade assembly is less than optimal and does not provide very precise cutting especially given the fact that the valve is made of both soft and hard tissue because it is heavily calcified or contains fibrotic tissue. Thus, the blades may buckle or bind as they alternately contact soft and hard tissue.

It is also presumed that pressure must be exerted on the blades. Control of this pressure and the control of the rotation rate, however, is not disclosed in the '685 patent. There is no margin for error in the resection procedure. If too much tissue is cut in certain areas, for example, the aorta can be permanently damaged. Moreover, the existing valve typically fails because of calcification of the valve resulting in stenosis or insufficiency. Using cutting blades for valve resection and an improper orientation or improper pressure on the cutting blades or the wrong rate of rotation can result in too little or too much tissue removal and/or imprecise cutting and/or blade buckling or binding as the blades alternately contact soft and hard (calcified) tissue.

Other relevant art includes the following, also included herein by this reference. Published Patent Application No. U.S. 2002/0095116 A1 discloses an aortic filter, an artery filter, and a check valve attached to the distal end of a canula for resecting an aortic valve from within the aorta. The mechanism for resecting the aortic valve, however, is not disclosed. U.S. Pat. No. 6,287,321 also discloses a percutaneous filtration catheter. U.S. Pat. No. 5,554,185 discloses an inflatable prosthetic cardiovascular valve but does not disclose any specific method of resecting the existing or native valve.

U.S. Pat. No. 6,425,916 discloses a percutaneous approach with a valve displacer for displacing and holding the native valve leaflets open while a replacement valve is expanded inside the native valve. In this way, the native valve does not need to be resected. In many cases, however, such a procedure can not be carried out due to the poor condition of the native valve. And, because the native valve occupies space, the largest aperture possible by the replacement valve may not provide sufficient blood flow.

U.S. Pat. Nos. 6,106,515 and 6,485,485, also incorporated herein by this reference, disclose various expandable laser catheter designs.

SUMMARY OF THE INVENTION

It is therefore an object of this invention to provide a more precise tissue cutting apparatus for endovascular heart valve replacement.

It is a further object of this invention to provide such a tissue cutter which is more effective than prior art blade type tissue cutters.

It is a further object of this invention to provide a tissue cutter which provides effective resection even if the valve is heavily calcified or has fibrotic tissue.

It is a further object of this invention to provide such a tissue cutter which does not require a high rate of rotation.

It is a further object of this invention to provide such a tissue cutter which eliminates the need for precise pressure control.

It is a further object of this invention to provide a mechanism which endovascularly supports the valve leaflets during resection.

The invention results from the realization that a more effective and more precise tissue cutting apparatus for endovascular heart valve replacement is effected by supporting the valve leaflets during resection using an expandable balloon advanced to the ventricular side of the valve. Various novel tissue ablation subassemblies are also disclosed as alterations to cutting blades.

This invention features an endovascular tissue removal system comprising an expandable mechanism introduceable to the ventricular side of a valve to support the leaflets of the valve in a closed position and a tissue removal device advanceable to the leaflets and configured to resect the leaflets as they are supported by the expandable mechanism.

In one embodiment, the tissue removal device includes a lumen connected to a source of ablation energy and further including an absorptive surface on the expandable mechanism for absorbing the ablation energy or a reflection surface for reflecting energy. The expandable mechanism is preferably a balloon.

In one example, the tissue removal device includes a lumen with a rotatable terminal hub advanceable in vasculature, at least one fiber extending from the hub for ablating tissue, and a second expandable mechanism connected to the fiber for biasing it into position for precisely ablating tissue as the hub rotates. There may be a plurality of fibers extending from the hub and connected to the second expandable mechanism so that the plurality of fibers can be spread apart for tissue ablation and also collapsed together for vascular insertion and removal. The second expandable mechanism is preferably a circumferentially expanding balloon. There may be two balloons, one inside and one outside of the distal end of the fiber. Typically, the lumen includes an inflation conduit therein connected to the balloon. The fiber may be an optical fiber connected to a source of laser energy or a waveguide connected to a source of laser energy.

Further included may be a tissue trap device surrounding the expandable mechanism. Typically, the fiber includes an angled distal portion. Also included may be a mirror for redirecting the ablation energy.

In another embodiment, the tissue removal device includes a lumen including a distal steerable tip portion extending from a joint portion, registration means for holding the joint portion fixed in place in the vasculature, and a source of ablation energy in communication with the lumen whereby tissue can be resected by ablation energy as the tip portion is steered within the vasculature. In one example, the registration means includes a second inflatable balloon about the joint portion, the source of ablation energy is a laser, the distal steerable tip portion includes a deflectable tip catheter, and there is an optical fiber inside the deflectable tip catheter and connected to the laser. An expandable barrier may be provided for trapping any debris resected.

Another tissue removal device includes a fiber advanceable within vasculature to ablate tissue, an outer expandable balloon, and an inner expandable balloon spaced from the outer expandable balloon forming a space within which the fiber travels to resect tissue. In one version, the outer expandable balloon is a portion of a tissue trap device and the distal end of the fiber is angled.

A method of endovascularly removing a heart valve in accordance with this invention comprises introducing an expandable mechanism to the ventricular side of the valve, expanding the mechanism to support the leaflets of the valve in a closed position, and resecting the leaflets of the valve as they are supported by the expandable mechanism.

Resecting typically includes directing ablative energy at the leaflets. A lumen is introduced within the vasculature of a patient to a situs proximate a heart valve to be resected, ablative energy is introduced into the lumen, and the lumen is rotated to resect the heart valve.

In another method, a lumen is endovascularly introduced with a distal steerable tip portion to a position proximate a valve to be resected, the lumen is registered in place in the vasculature, ablation energy is directed through the lumen, and the distal steerable tip portion is steered to resect the valve.

BRIEF DESCRIPTION OF THE DRAWINGS

Other objects, features and advantages will occur to those skilled in the art from the following description of a preferred embodiment and the accompanying drawings, in which.

DISCLOSURE OF THE PREFERRED EMBODIMENT

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings.

Figure 1:
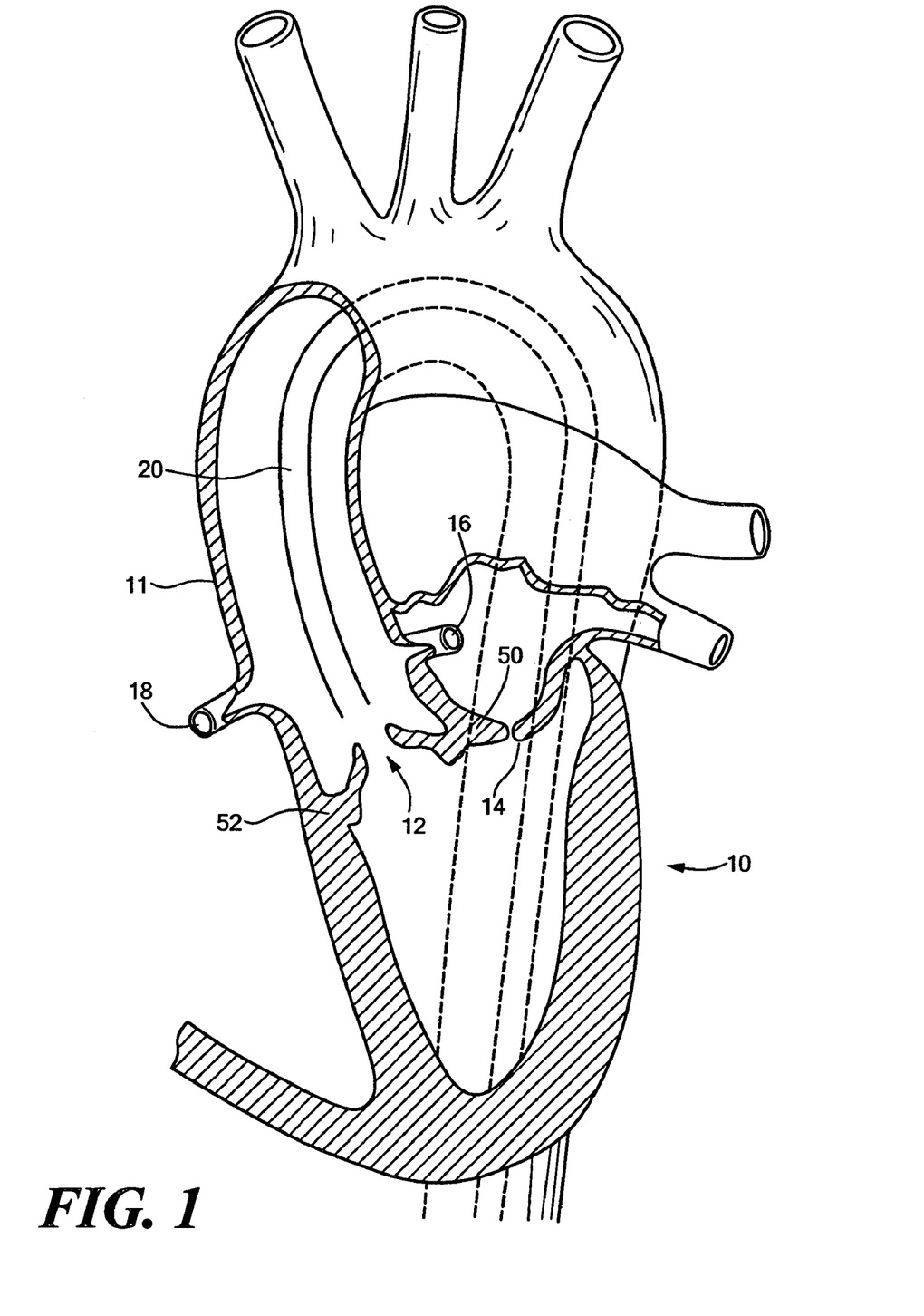
FIG. 1 is a schematic view showing a typical human heart.

FIG. 1 schematically shows heart 10 with aorta 11, aortic valve 12, mitral valve 14, and coronary arteries 16 and 18. The idea behind percutaneous valve replacement surgery is to deliver a catheter 20 proximate valve 12 to resect it and to secure a replacement prosthetic valve in place. Resecting the native valve, however, is problematic. Those skilled in the art have devised inflatable barriers such as barrier 30, FIG. 2 used to trap tissue during resection. See also U.S. Pat.

Figure 2:
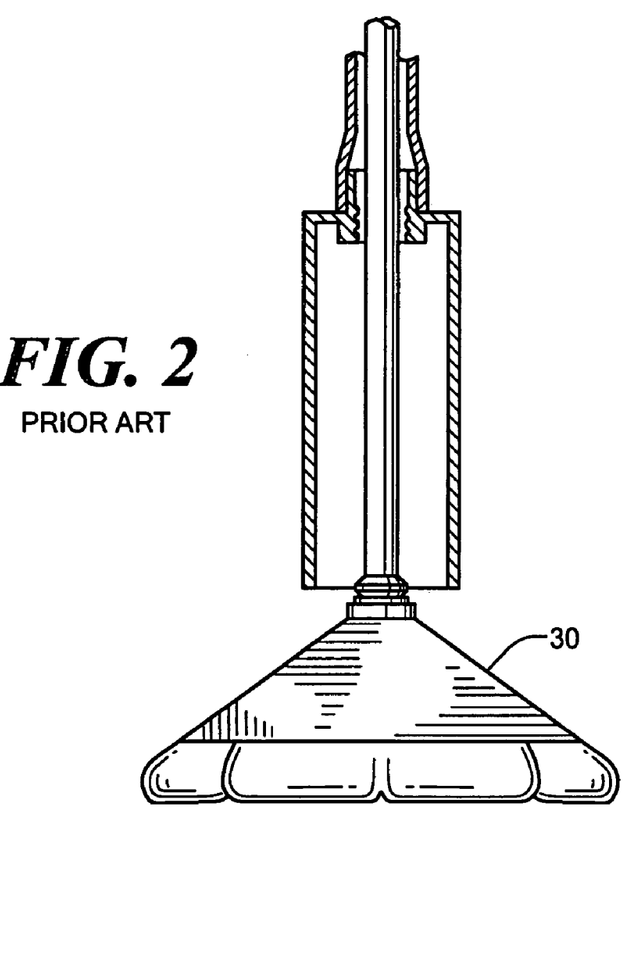
FIG. 2 is a schematic view of a prior art inflatable barrier used in endovascular aortic valve replacement procedures.

No. 6,287,321 and Published Patent Application No U.S. 2002/0095116 A1. Barrier 30 traps any tissue cut during valve resection.

Figure 3:
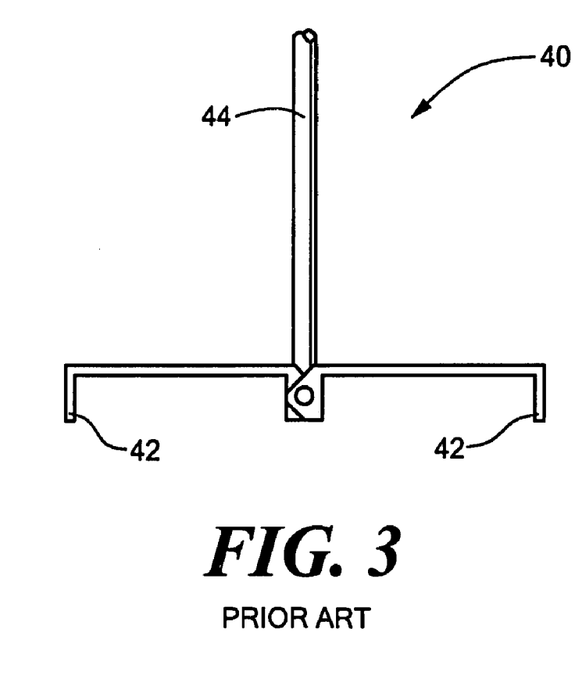
FIG. 3 is a schematic view showing a prior art tissue cutter used in endovascular aortic valve replacement procedures.

But, the prior art teaches resection of the native valve tissue by tissue cutter 40, FIG. 3 with blades 42. Tissue cutter 40 is connected to shaft 44 rotated by a DC motor presumably at a very high rate of rotation in order to effect tissue cutting. It is also presumed that pressure must be exerted on the blades. Control of this pressure and the control of the rotation rate, however, is not disclosed in the '685 or '321 patents.

As shown in FIG. 1, there is no margin for error in the resection procedure. If too much tissue is cut in areas 50 or 52, for example, the aorta can be permanently damaged. Moreover, existing valve 12 (or 14) typically fails because of calcification of the valve resulting in stenosis or insufficiency. Using cutting blades for valve resection and an improper orientation or improper pressure on the cutting blades or the wrong rate of rotation can result in too little or too much tissue removal and/or imprecise cutting and/or blade buckling or binding as the blades alternately contact soft and hard (calcified) tissue.

The problem is so profound that some skilled in the art have attempted to eliminate native valve resection and instead theorize that a prosthetic valve can be expanded directly within native valve 12 (or 14) using a valve displacer to hold the native valve open. As delineated above, however, due to the condition of the native valve, such a procedure is not always possible or effective.

Figure 4:
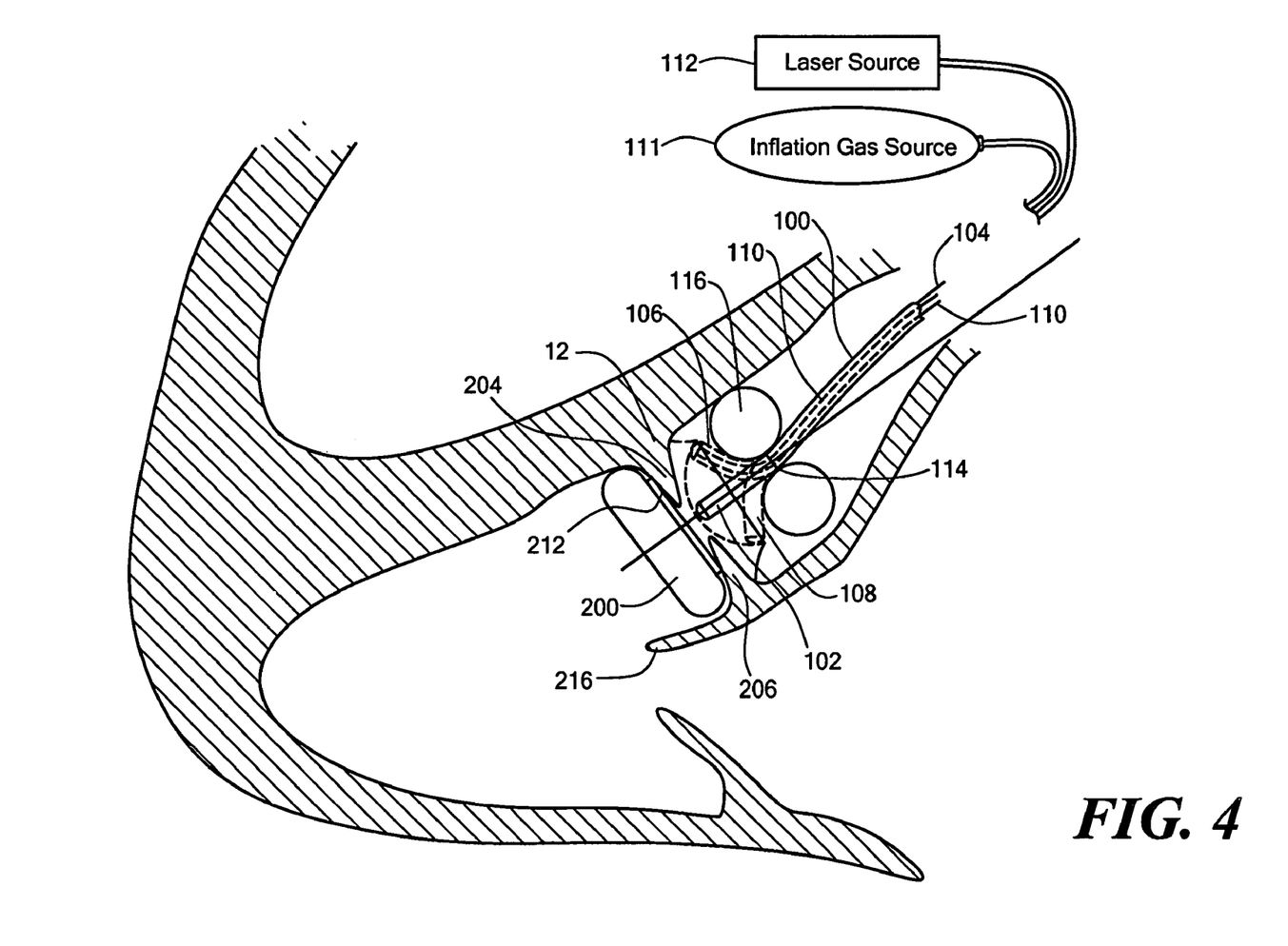
FIG. 4 is a schematic three-dimensional view showing the primary components associated with one embodiment of endovascular tissue removal device of the subject invention.

In the subject invention, more precise tissue cutting is effected even if native valve 12, FIG. 4 is heavily calcified or has fibrotic tissue. One endovascular tissue removal device of this invention includes lumen 100 advanceable within the patient's vascular with distal steerable tip portion 102, typically a deflectable tip catheter which employs wire 104 to maneuver tip portion as shown in phantom at 106 and 108. One such deflectable tip catheter is sold by Cardima of Freemont, Calif. under the trademark Naviport®. Optical fiber 110 is disposed in catheter 100. The distal end of optical fiber 110 extends to, nearly to, or slightly beyond the distal end of catheter 100. In the preferred embodiment, optical fiber 110 is connected to laser source 112. Other sources of ablation energy, however, may be used. The subject invention also features registration means for holding joint portion 114 of lumen 100 fixed in place in the vasculature for precise steering of distal steerable portion 102 to resect valve 12 with laser energy. In the preferred embodiment, the registration means includes inflatable balloon 116 about joint portion 114 inflated with gas from source 111.

Lower balloon 200 is disposable on the ventricular side of the heart valve under leaflets 204 and 206. Balloon 200 is connected to an inflation conduit which extends within multi-lumen catheter 100. An outer suction conduit may include a port for withdrawing tissue. Balloon 200 performs several important functions. First, it supports leaflets 204 and 206 of the valve as they are pushed closed by the tissue removal device before cutting for more accurate cutting. Balloon 200 with laser energy absorption or reflection layer 212 also prevents inadvertent cutting of any portion of mitral valve 216.

A complete system may include an expandable barrier such as barrier 30, FIG. 2 to trap tissue during resection. In one example, the subject invention is used as follows. Device capsule 29, FIG. 2 is delivered to the site and barrier 30 expanded. Lumen 100, FIG. 4 is then delivered within tube 127 and balloons 200 and 116 deployed and inflated. The physician then manipulates wire 104 to steer tip portion 102 as shown at 106 and 108 to resect valve 12 using laser energy from source 112. After full resection, balloons 200 and 116 are deflated and lumen 100 removed. The tissue is then sucked out of tube 27 and barrier 30 is brought back into capsule 29 which is then withdrawn. Finally, a valve introducer is advanced to the site and the replacement valve installed.

In this way, the problems associated with prior art blade type tissue cutters are eliminated and tissue cutting is far more precise by the use of optical fiber 110 within deflectable tip catheter 100 and expandable balloon 116 which registers the assembly inside the heart for resection by laser ablation as the deflectable tip portion steers the distal end of optical fiber 110.

Figure 5:
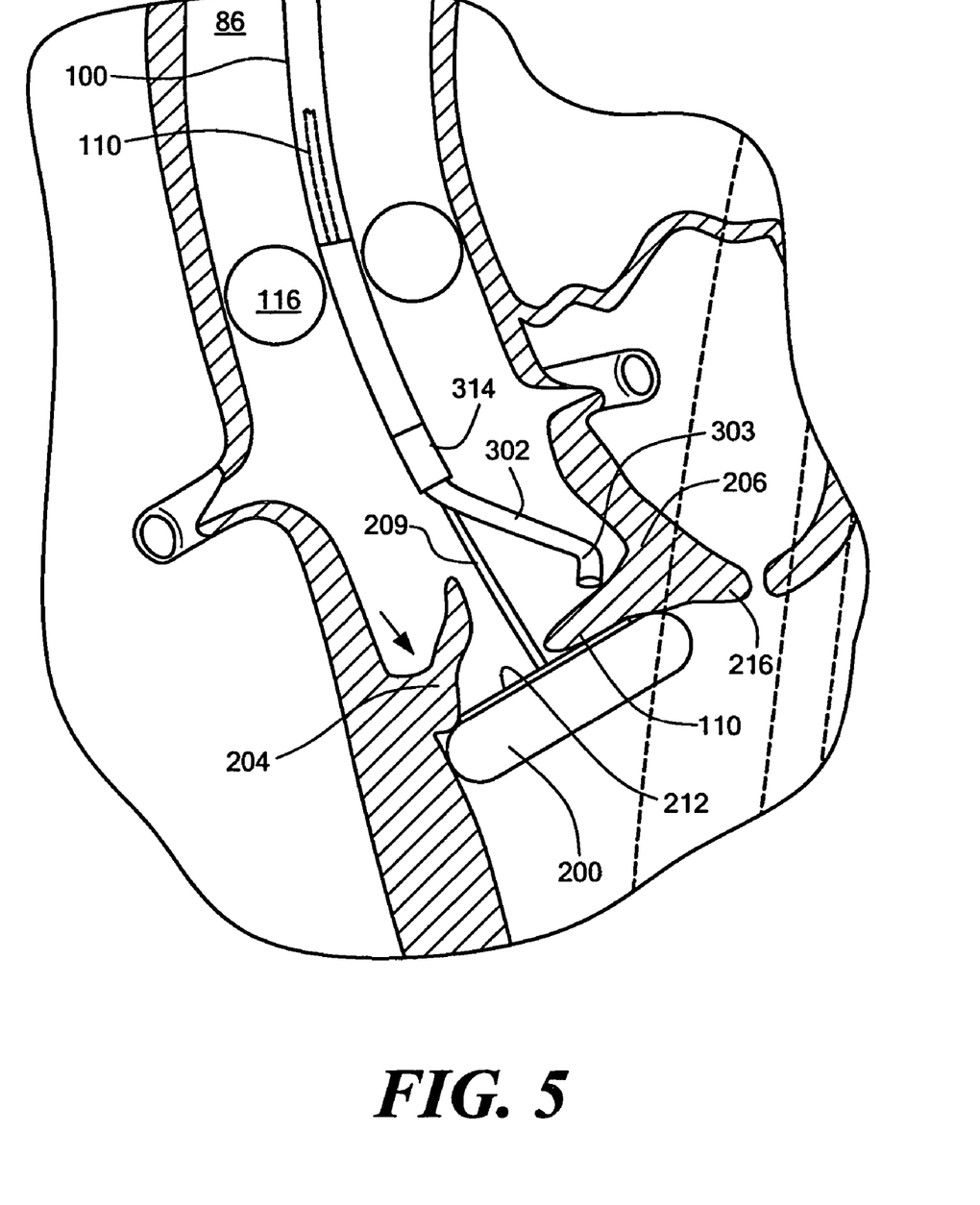
FIG. 5 is a schematic three-dimensional view showing another embodiment of the tissue removal device of the subject invention.

In the embodiment of FIG. 5, tissue removal device 302 is includes angled distal tip 303 connected to hub 314 supported by balloon 116. Angled distal tip 303 is rotated to resect valve leaflets 204 and 206 supported by balloon 200.

Figure 6:
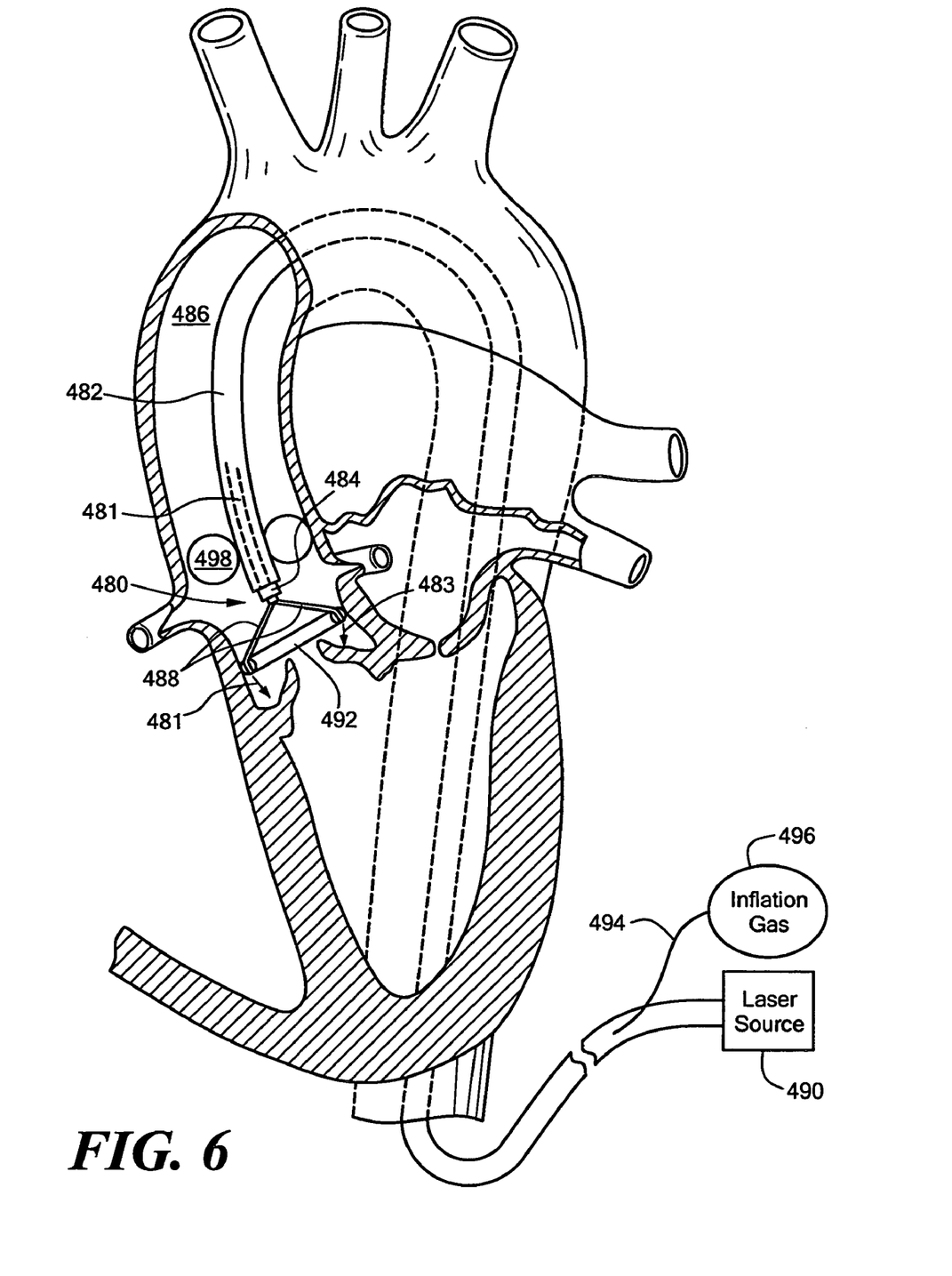
FIG. 6 is a schematic view of a typical human heart depicting the precise nature of the tissue ablation possible with one version of the endovascular tissue removal device of the subject invention.

In another embodiment, the endovascular tissue removal device 480, FIG. 6 includes lumen 482 (e.g. an optical fiber or waveguide or a catheter enclosing an optical fiber or waveguide) with rotatable terminal hub 484 advanced in vasculature 486. At least one but preferably a plurality of fibers 488 (optical fibers or waveguides) extend from hub 484 for ablating tissue—not by blade contact as in the prior art discussed above, but preferably by laser ablation energy. Thus, in the preferred embodiment, optical fiber or waveguide 481 in lumen 482 is connected to laser source 490. Other sources of ablation energy may also be used. The tissue removal device also includes an expandable mechanism connected to the fibers for biasing them into position for precisely ablating tissue as hub 484 is rotated. In the preferred embodiment, the expandable mechanism is circumferentially expanding balloons 491 and 492, FIG. 7 which spread apart the fibers for ablation and which collapse them together for vascular insertion and removal. Inflation conduit 494, FIG. 6 also in lumen 484 along with the optical fiber connects inflation gas source 496 to balloons 491 and 492 and also to optional registration balloon 498 which registers hub 484 in place for rotation. Thus, lumen 482 is typically a multi-lumen catheter.

Figure 7:
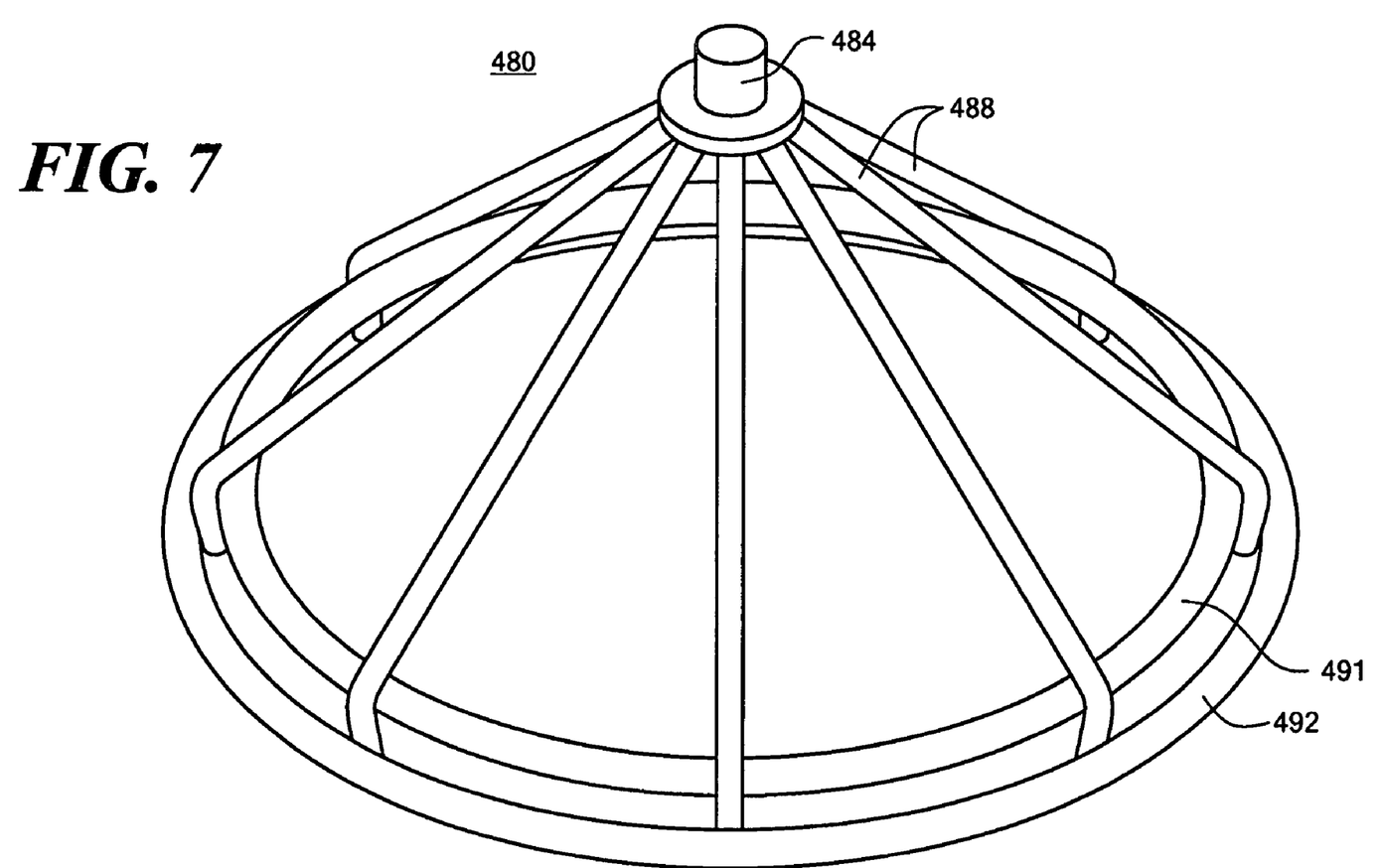
FIG. 7 is a schematic three-dimensional view showing the primary components associated with one endovascular tissue removal device in accordance with the subject invention.
Figure 8:
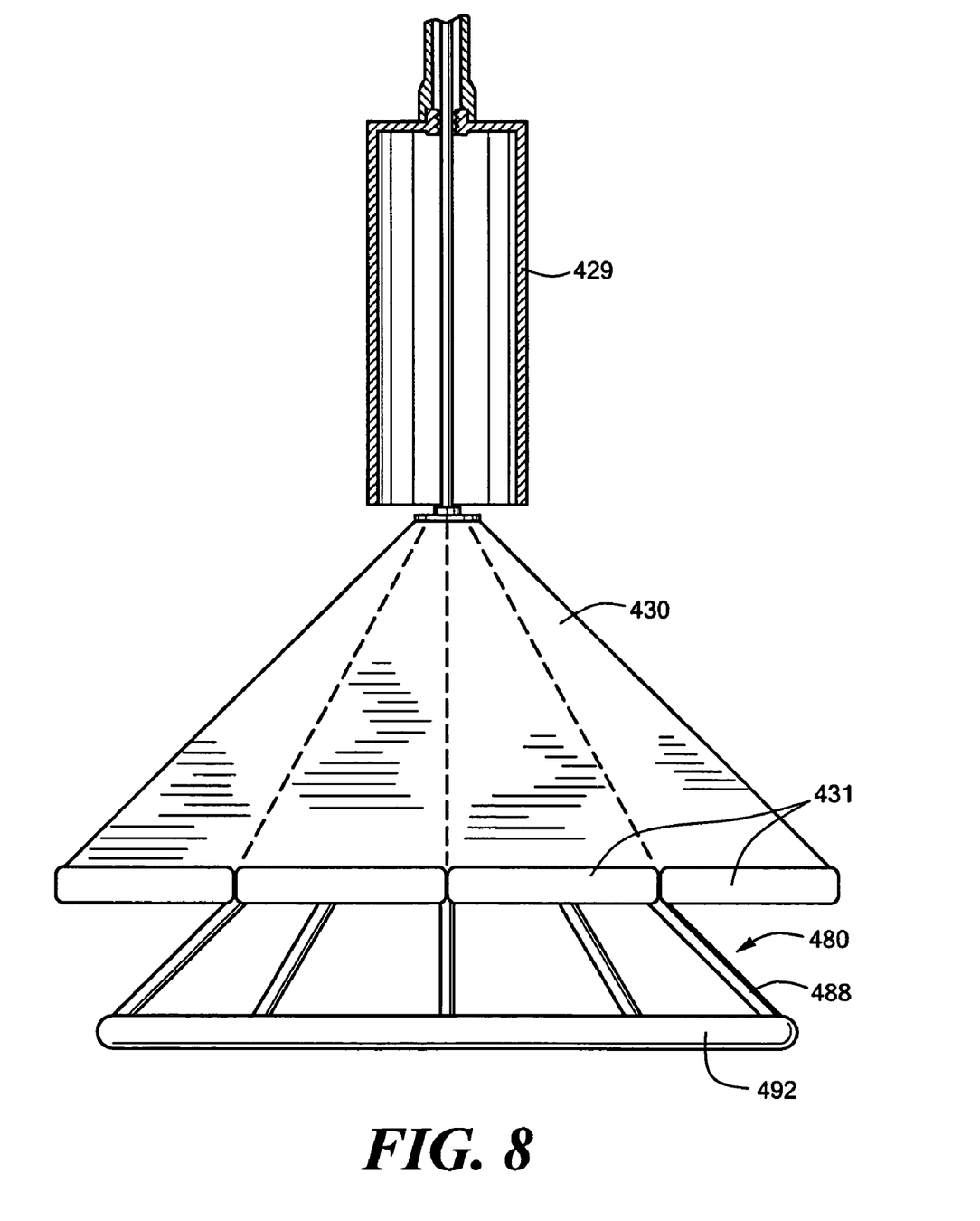
FIG. 8 is a schematic view showing another embodiment of an endovascular tissue removal device in accordance with the subject invention rotatable within a tissue barrier device.
Figure 9:
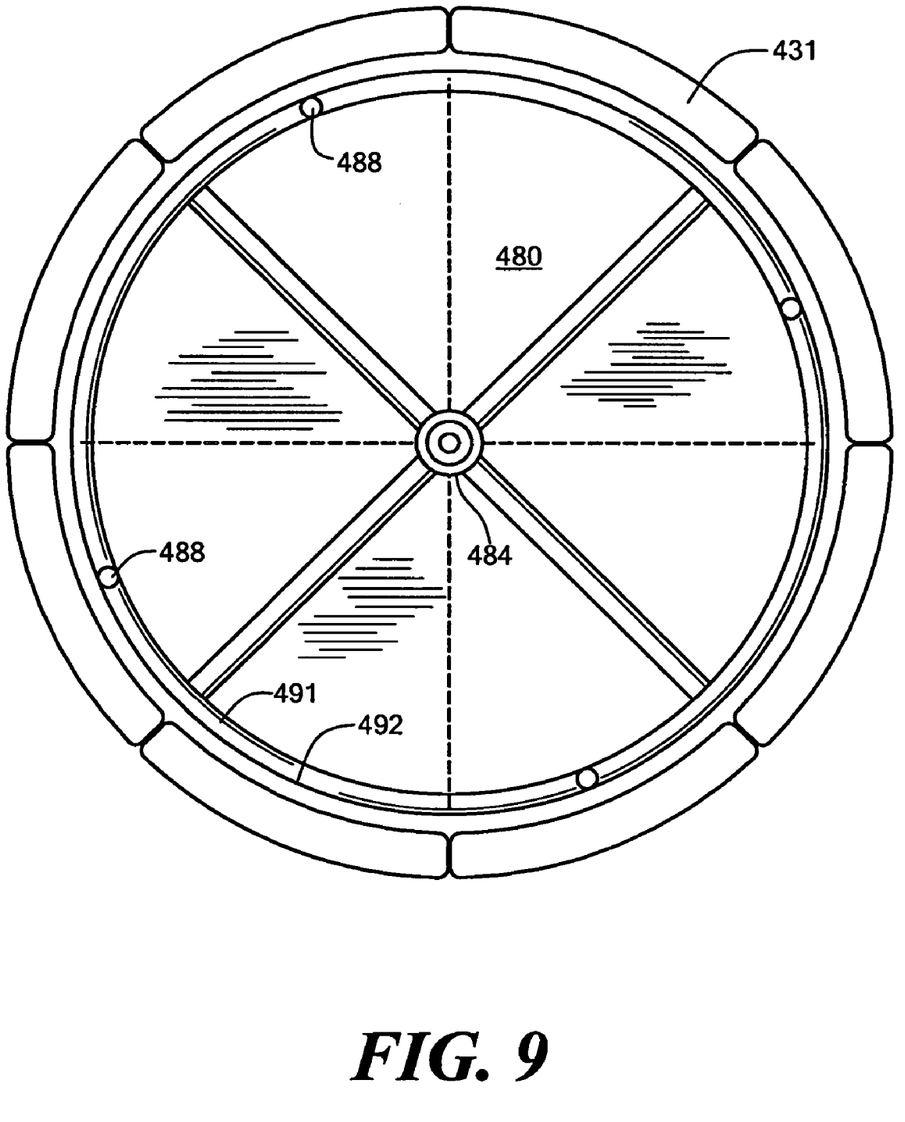
FIG. 9 is a bottom plan view of the subsystem shown in FIG. 8.

In FIG. 6-7, spreader balloons 491 and 492 are shown to support the distal end of each optical fiber 488. In FIGS. 8-9 endovascular tissue removal device 480 is used in conjunction with inflatable tissue barrier device 430 and is collapsible within device capsule 429. In one example, the subject invention is used as follows. Device capsule 429 is delivered to the site and balloon segments 431 of barrier 430 expanded. Endovascular tissue removal device 480 still in its collapsed state is then pushed out of device capsule 429 inside of barrier 430 and balloon 492 along with registration balloon 498 (FIG. 6) are inflated. The physician then rotates hub 484 to resect the native valve using laser energy from source 490. After full recession, balloons 491 and 492 are deflated and tissue removal device 480 is brought back within device capsule 429. Tissue is then sucked out of lumen 482 and barrier 430 is brought back into device capsule 429 which is then withdrawn. Finally, a valve introducer is advanced to the site and a replacement valve is installed. Alternately, if there are numerous closely spaced fibers 488, FIG. 7, rotation of the hub may not be required to resect the native valve.

In this way, the problem associated with prior art blade type tissue cutters are eliminated and tissue cutting is more precise by the use of electromagnetic energy in combination with the expandable balloon which spreads apart the plurality of optical fibers 488 and registration balloon 498 which registers the assembly inside the heart for resection typically as hub 484 rotates. The distal ends of optical fibers 488 are preferably precisely oriented to resect only valve tissue as shown by vectors 481 and 483, FIG. 6.

Figure 10:
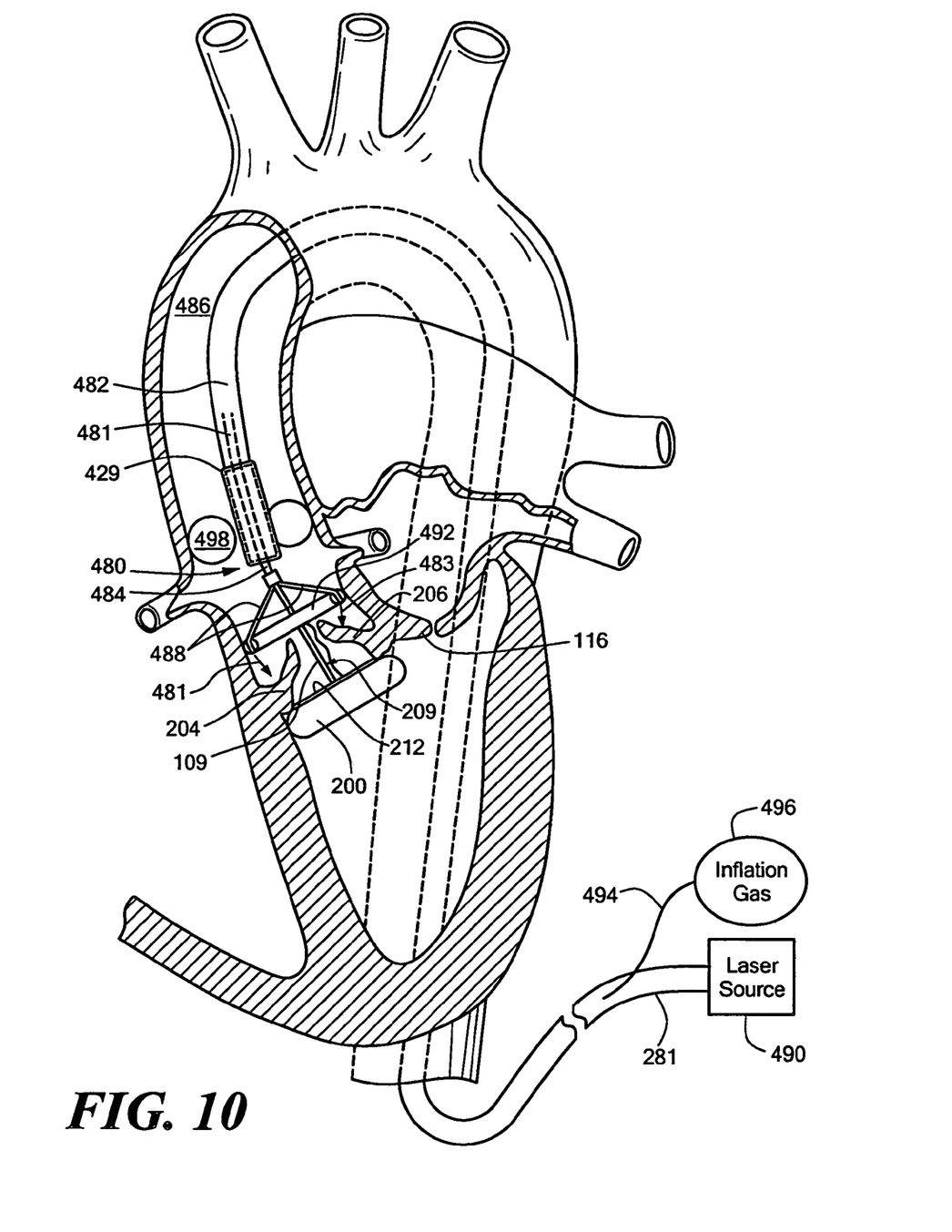
FIGS. 10-11 are schematic cross-sectional views showing, in one embodiment, a more complete valve resection system in accordance with the subject invention.
Figure 11:
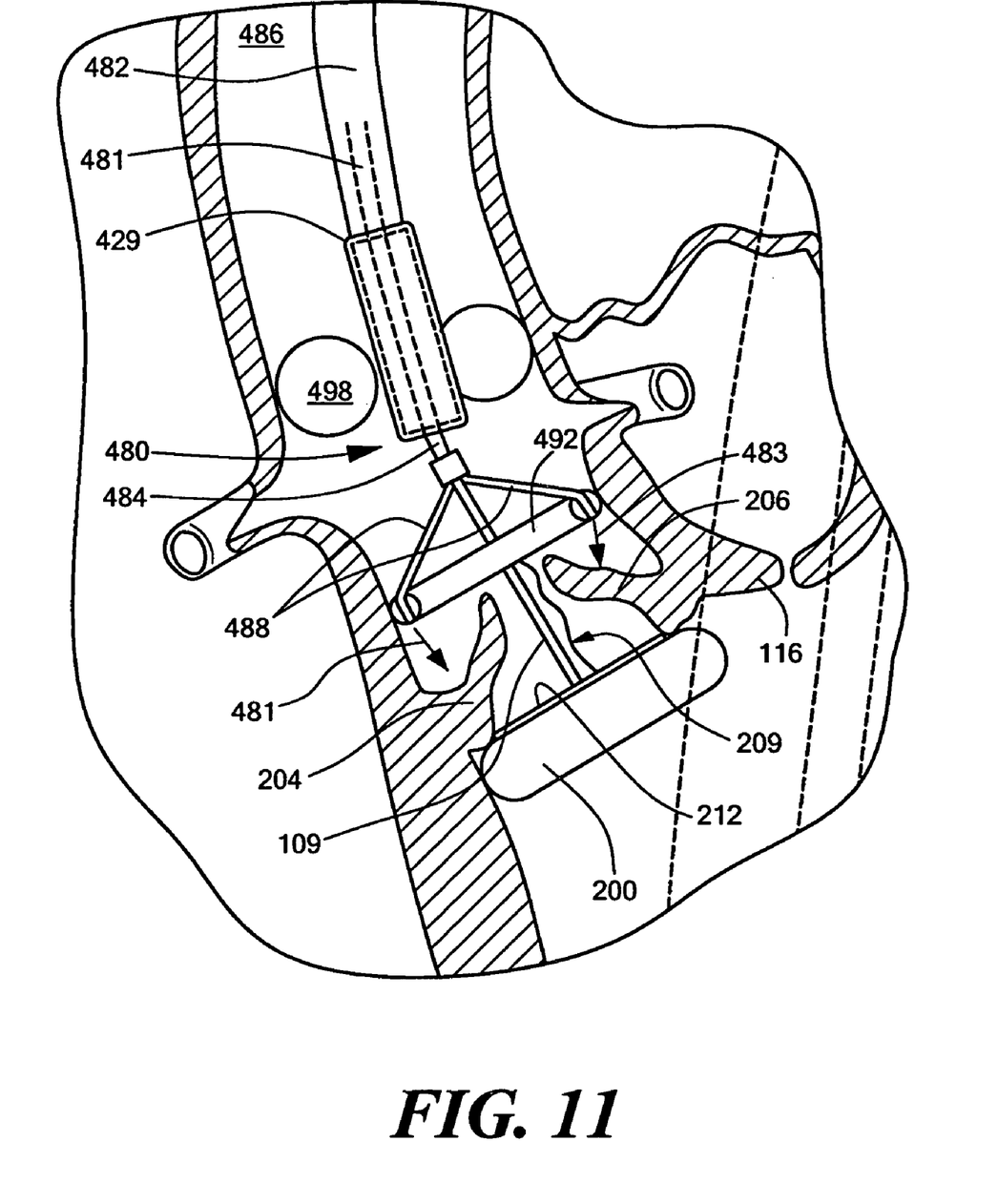
Figure 12:
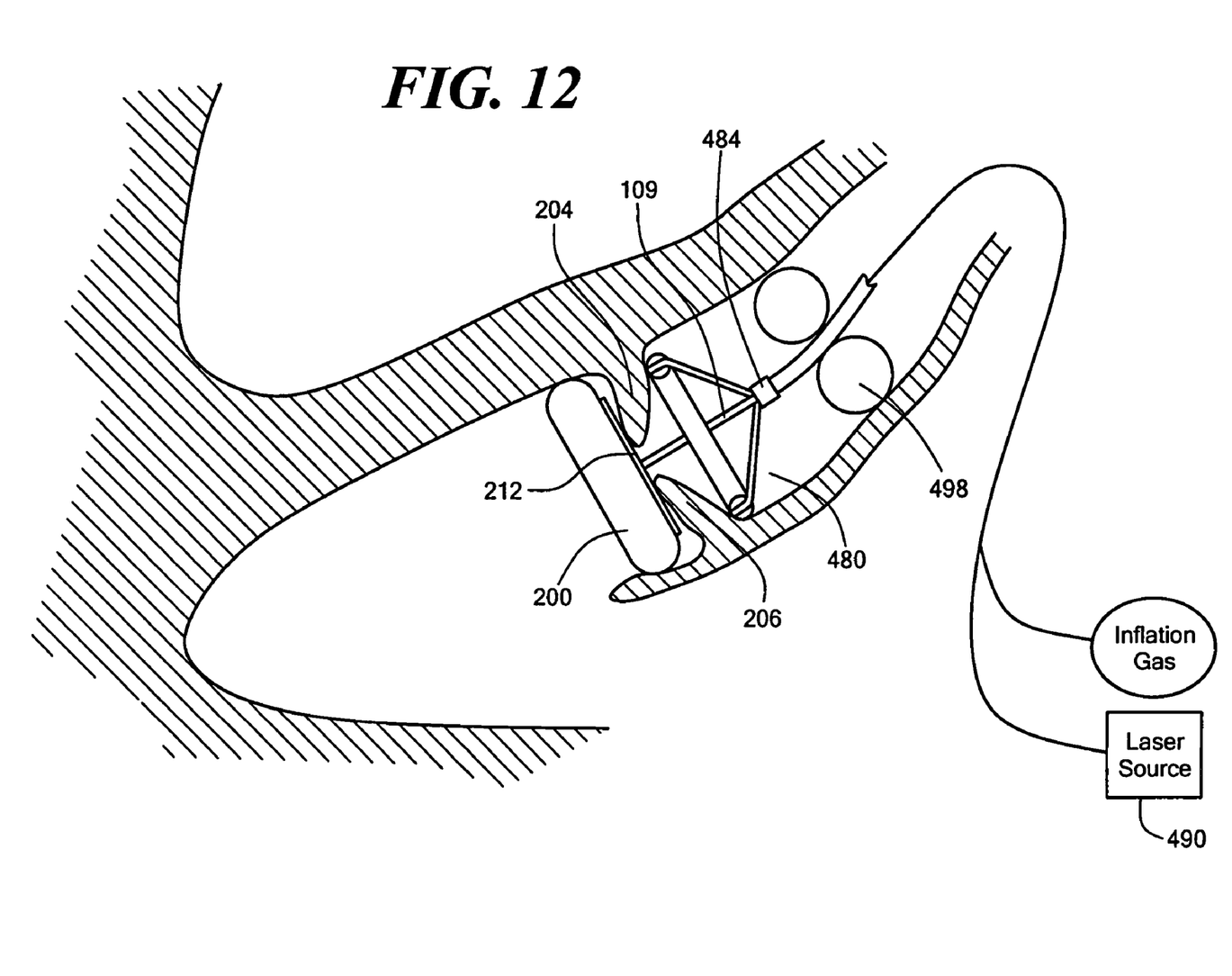
FIG. 12 is another schematic cross-sectional view showing how the lower balloon of the system shown in FIGS. 10-11 supports the valve leaflets.

A more complete system is shown in FIGS. 10-11 including device capsule 429 (see FIGS. 2 and 8), the tissue removal device (see FIG. 7), and lower balloon 200 disposable on the ventricular side of the heart valve under leaflets 204 and 206. Balloon 200 is connected to inflation conduit 109 which extends within multi-lumen catheter 281. An outer suction conduit may include a port for withdrawing tissue. Balloon 200 performs several important functions. First, it supports leaflets 204 and 206 of the valve as they are pushed closed by tissue removal device 80 as shown in FIG. 12 before cutting for more accurate cutting. Balloon 200 with laser energy absorption or reflection layer 212 also prevents in advertent cutting of any portion of mitral valve 116.

Figure 13:
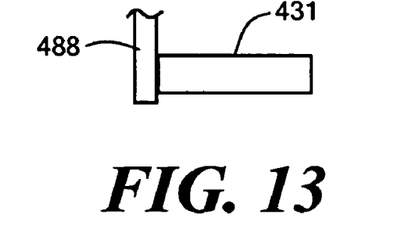
FIG. 13 is a schematic cross-sectional view showing an embodiment of a tissue cutting subsystem in accordance with the subject invention wherein the fiber or fibers are attached to and rotate with the tissue trap subsystem.
Figure 14:
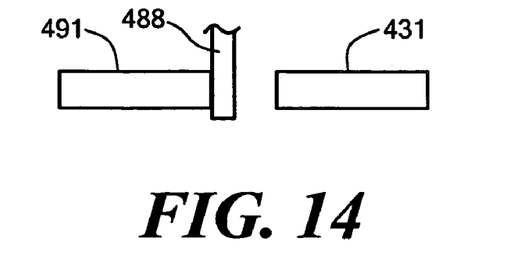
FIG. 14 is a schematic cross-sectional view showing another example of the subject invention where the fiber or fibers are rotatable within the tissue trap device.
Figure 15:
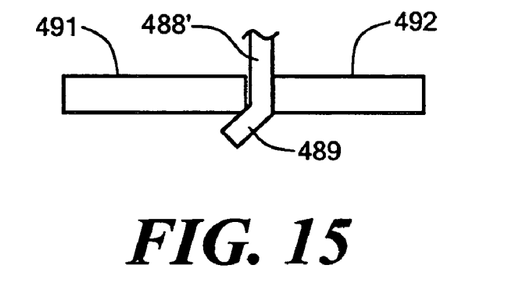
FIG. 15 is a schematic cross-sectional view showing an embodiment of the tissue cutter of the subject invention wherein the fiber includes an angled distal tip portion.
Figure 18:
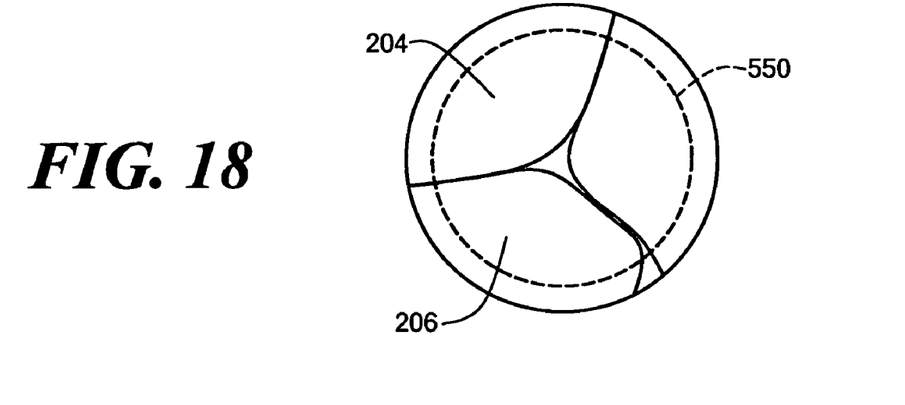
FIG. 18 is a schematic top view showing a tissue cutting line possible in accordance with the subject invention.

In still another embodiment, optical fiber 488, FIG. 13 is fixed to balloon 431 of the tissue barrier device and the tissue barrier device is rotated to resect the native valve. In the example of FIG. 14, optical fiber 488 is fixed to single balloon 491 of the tissue cutter and the tissue cutter is rotated within the barrier device to resect the native valve. In the embodiment of FIG. 15, optical fiber 488' is disposed between inner balloon 491 and outer balloon 492 of the tissue cutter device and includes angled distal tip portion 489 to ensure laser energy does not cut areas 50 or 52, FIG. 1. The resulting cut line is shown at 550 in FIG. 18.

Figure 16:
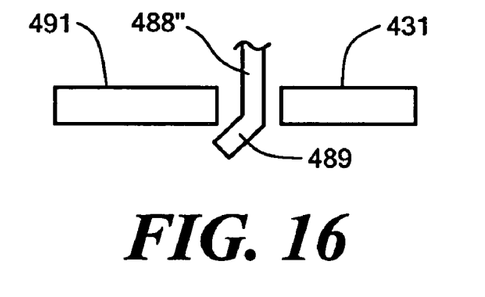
FIG. 16 is a schematic cross-sectional view showing still another embodiment of the tissue cutter subsystem of the subject invention wherein the fiber rotates between an inner balloon and the outer balloon.

In the embodiment of FIG. 16, optical fiber 488" is freely rotatable within the spaces formed between balloon 491 of the tissue removal device and balloon 431 of the tissue barrier device. In this embodiment, it is also preferable that optical fiber 488" includes angled distal tip portion 489.

Figure 17:
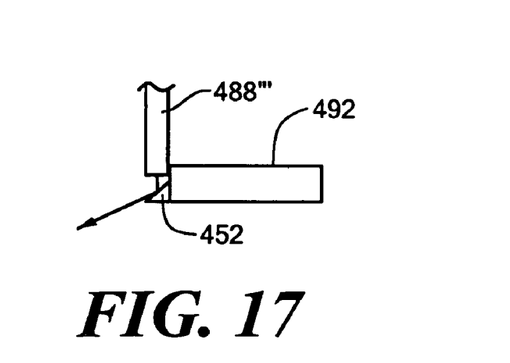
FIG. 17 is a schematic cross-sectional view showing another example of a tissue cutter device in accordance with the subject invention wherein the fiber is attached to a balloon with a mirror for redirecting the laser energy inward.

In the embodiment of FIG. 17, optical fiber 488''' is attached to the inside of balloon 492 of the tissue cutter device which is rotated to resect the native valve. But, the laser energy is directed inward due to mirror 452 on or integral with balloon 492.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

Other embodiments will occur to those skilled in the art and are within the following claims:

What is claimed is:

1. An endovascular tissue removal system comprising:
    an expandable mechanism introduceable to the ventricular side of a valve to support the leaflets of the valve in a closed position; and
    a tissue removal device advanceable to the leaflets and configured to resect the leaflets as they are supported by the expandable mechanism.

2. The system of claim 1 in which the tissue removal device includes a lumen connected to a source of ablation energy and further including an absorptive surface on the expandable mechanism for absorbing the ablation energy or a reflection surface for reflecting the energy.

3. The system of claim 1 in which the expandable mechanism is a balloon.

4. The system of claim 1 in which the tissue removal device includes:
    a lumen including a rotatable terminal hub advanceable in vasculature,
    at least one fiber extending from the hub for ablating tissue, and
    a second expandable mechanism connected to the fiber for biasing it into position for precisely ablating tissue as the hub rotates.

5. The system of claim 4 in which there are a plurality of fibers extending from the hub and connected to the second expandable mechanism so that the plurality of fibers can be spread apart for tissue ablation and also collapsed together for vascular insertion and removal.

6. The system of claim 4 in which the second expandable mechanism is a circumferentially expanding balloon.

7. The system of claim 6 in which there are two balloons, one inside and one outside of the distal end of the fiber.

8. The system of claim 6 in which the lumen includes an inflation conduit therein connected to the balloon.

9. The system of claim 4 in which the fiber is an optical fiber connected to a source of laser energy.

10. The system of claim 4 in which the fiber is a waveguide connected to a source of laser energy.

11. The system of claim 4 further including a tissue trap device surrounding the expandable mechanism.

12. The system of claim 4 in which the fiber includes an angled distal portion.

13. The system of claim 4 further including a mirror for redirecting the ablation energy.

14. The system of claim 1 in which the tissue removal device includes:
    a lumen including a distal steerable tip portion extending from a joint portion,
    registration means for holding the joint portion fixed in place in the vasculature, and
    a source of ablation energy in communication with the lumen whereby tissue can be resected by ablation energy as the tip portion is steered within the vasculature.

15. The system of claim 14 in which the registration means includes a second inflatable balloon about the joint portion.

16. The system of claim 14 in which the source of ablation energy is a laser.

17. The system of claim 16 in which the distal steerable tip portion includes a deflectable tip catheter.

18. The system of claim 17 in which there is an optical fiber inside the deflectable tip catheter and connected to the laser.

19. The system of claim 14 further including an expandable barrier for trapping any debris resected.

20. The system of claim 1 in which the tissue removal device includes:
    a fiber advanceable within vasculature to ablate tissue,
    an outer expandable balloon, and
    an inner expandable balloon spaced from the outer expandable balloon forming a space within which the fiber travels to resect tissue.

21. The system of claim 20 in which the outer expandable balloon is a portion of a tissue trap device.

22. The system of claim 20 in which the distal end of the fiber is angled.

23. An endovascular tissue removal system comprising:
    an expandable mechanism introduceable to the ventricular side of a valve to support the leaflets of the valve in the closed position; and a tissue removal device advanceable to the leaflets and configured to resect the leaflets as they are supported by the expandable mechanism, the tissue removal device including:
  a lumen including a rotatable terminal hub advanceable and vasculature,
  at least one fiber extending from the hub for ablating tissue, and
  a second expandable mechanism connected to the fiber for biasing it into position for precisely ablating tissue as the hub rotates.

24. An endovascular tissue removal system comprising:
an expandable mechanism introduceable to the ventricular side of a valve to support the leaflets of the valve in the closed position; and
a tissue removal device advanceable to the leaflets and configured to resect the leaflets as they are supported by the expandable mechanism the tissue removal device including:
  a lumen including a distal steerable tip portion extending from a joint portion,
  registration means for holding the joint portion fixed in place in the vasculature, and
  a source of ablation energy in communication with the lumen whereby tissue can be resected by ablation energy as the tip portion is steered within the vasculature.

25. An endovascular tissue removal system comprising:
an expandable mechanism introduceable to the ventricular side of a valve to support the leaflets of the valve in the closed position; and
a tissue removal device advanceable to the leaflets and configured to resect the leaflets as they are supported by the expandable mechanism, the tissue removal device including:
  a fiber advanceable within vasculature to ablate tissue,
  an outer expandable balloon, and
  an inner expandable balloon spaced from the outer expandable balloon forming a space within which the fiber travels to resect tissue.

26. A method of endovascularly removing a heart valve, the method comprising:
  introducing an expandable mechanism to the ventricular side of the valve;
  expanding the mechanism to support the leaflets of the valve in a closed position; and
  resecting the leaflets of the valve as they are supported by the expandable mechanism.

27. The method of claim 26 in which resecting includes directing ablative energy at the leaflets.

28. The method of claim 27 in which resecting includes:
  introducing a lumen within the vasculature of a patient to a situs proximate a heart valve to be resected,
  introducing ablative energy into the lumen, and
  rotating the lumen to resect the heart valve.

29. The method of claim 27 in which resecting includes:
  endovascularly introducing a lumen with a distal steerable tip portion to a position proximate a valve to be resected,
  registering the lumen in place in the vasculature,
  directing ablation energy through the lumen, and
  steering the distal steerable tip portion to resect the valve.

* * * * *